United States Patent
Ishida et al.

(10) Patent No.: US 11,255,836 B2
(45) Date of Patent: Feb. 22, 2022

(54) SOIL ESTIMATION DEVICE, SOIL ESTIMATION METHOD, AND COMPUTER-READABLE RECORDING MEDIUM

(71) Applicant: NEC CORPORATION, Tokyo (JP)

(72) Inventors: Kosuke Ishida, Tokyo (JP); Shinji Oominato, Tokyo (JP); Masami Sakaguchi, Tokyo (JP); Shunsuke Akimoto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 386 days.

(21) Appl. No.: 16/338,372

(22) PCT Filed: Mar. 22, 2017

(86) PCT No.: PCT/JP2017/011467
§ 371 (c)(1),
(2) Date: Mar. 29, 2019

(87) PCT Pub. No.: WO2018/061255
PCT Pub. Date: Apr. 5, 2018

(65) Prior Publication Data
US 2020/0025742 A1    Jan. 23, 2020

(30) Foreign Application Priority Data
Sep. 30, 2016    (JP) .............................. JP2016-195105

(51) Int. Cl.
*G01N 33/24*    (2006.01)
*A01B 79/00*    (2006.01)
*G06T 11/20*    (2006.01)

(52) U.S. Cl.
CPC ......... *G01N 33/246* (2013.01); *A01B 79/005* (2013.01); *G06T 11/206* (2013.01); *G01N 2033/245* (2013.01)

(58) Field of Classification Search
CPC ............ G01N 33/246; G01N 2033/245; A01B 79/005; G06T 11/206
(Continued)

(56) References Cited

U.S. PATENT DOCUMENTS

2007/0288167 A1 * 12/2007 Anderson ............ A01B 79/005
702/2
2014/0358486 A1   12/2014 Osborne
(Continued)

FOREIGN PATENT DOCUMENTS

JP    2005-052045 A    3/2005
JP    2005-085059 A    3/2005
(Continued)

OTHER PUBLICATIONS

English translation of JP2005085059. (Year: 2005).*
(Continued)

*Primary Examiner* — Michael P Nghiem
(74) *Attorney, Agent, or Firm* — Sughrue Mion, PLLC

(57) ABSTRACT

Provided are a soil estimation device, a soil estimation method and a program that are capable of improving the accuracy of estimation of a state in soil without increasing the number of sensors that detect the state in the soil. The soil estimation device 100 is provided with an estimated model generation unit 10. The estimated model generation unit 10 generates an estimated model based on at least one among geographical information that specifies a geographical feature of a field of interest and soil distribution information that specifies a soil distribution in the field. The estimated model is a model for estimating, from a measured value that indicates the state in the soil at one location within the field, the state in the soil at a location other than the one location.

7 Claims, 11 Drawing Sheets

(58) Field of Classification Search
USPC .............................................. 702/2
See application file for complete search history.

(56) References Cited

U.S. PATENT DOCUMENTS

2016/0247082 A1* 8/2016 Stehling ................. G06N 7/005
2019/0048556 A1* 2/2019 Kasahara ............... G01H 17/00

FOREIGN PATENT DOCUMENTS

| JP | 2006-038511 | A | 2/2006 |
| JP | 2007-252234 | A | 10/2007 |
| JP | 2013-074807 | A | 4/2013 |
| WO | 2016/130001 | A1 | 8/2016 |

OTHER PUBLICATIONS

English translation of JP2005052045. (Year: 2005).*
English translation of JP 2005085059, Mar. 2005. (Year: 2005).*
English translation of JP 2005052045, Mar. 2005. (Year: 2005).*
Moran et al., "Estimating soil moisture at the watershed scale with satellite-based radar and land surface models", Can. J. Remote Sensing, vol. 30. No. 5, pp. 805-826, 2004 (22 pages total).
Kheir et al., "Predictive mapping of soil organic carbon in wet cultivated lands using classification-tree based models: The case study of Denmark", Journal of Environmental Management, vol. 91 (2010) pp. 1150-1160 (11 pages total).
Beskow et al., "Soil erosion prediction in the Grande River Basin, Brazil using distributed modeling", Catena, vol. 79 (2009) pp. 49-59 (11 pages total).
Extended European Search Report dated Jul. 27, 2020, from the European Patent Office in Application No. 17855214.7.
International Search Report for PCT/JP2017/011467 dated Jun. 27, 2017 [PCT/ISA/210].

* cited by examiner

Height from reference plane: 20cm–30cm

Height from reference plane: 10cm–20cm

Height from reference plane: 0cm–10cm

Soil distribution information

Clay 80%, Sand 10%, Silt 10%

Clay 60%, Sand 15%, Silt 25%

Clay 40%, Sand 10%, Silt 30%

Clay 20%, Sand 50%, Silt 30%

Soil moisture sensor

Fig.6

| Grid position | Silt(%) | Sand(%) | Clay(%) | ..... | Slope (%) | Measured value (mm) | Calculated value (mm) |
|---|---|---|---|---|---|---|---|
| 1-(1) | 30 | 10 | 40 | | 2 | | 150 |
| 1-(2) | 23 | 12 | 50 | | 4 | | 200 |
| 1-(3) | 23 | 12 | 50 | | 4 | | 200 |
| ..... | | | | | | | |
| 3-(1) | 23 | 12 | 50 | | 4 | | 150 |
| 3-(2) | 25 | 15 | 60 | | 5 | | 250 |
| 3-(3) | 15 | 10 | 80 | | 7 | 300 | 300 |
| ..... | | | | | | | |
| 6-(1) | 30 | 10 | 40 | | 2 | | 150 |
| 6-(2) | 30 | 10 | 40 | | 2 | | 150 |
| ..... | | | | | | | |

SOIL ESTIMATION DEVICE, SOIL ESTIMATION METHOD, AND COMPUTER-READABLE RECORDING MEDIUM

CROSS REFERENCE TO RELATED APPLICATIONS

This application is a National Stage of International Application No. PCT/JP2017/011467 filed Mar. 22, 2017, claiming priority based on Japanese Patent Application No. 2016-195105 filed Sep. 30, 2016.

TECHNICAL FIELD

The present invention relates to a soil estimation device, a soil estimation method, and a computer-readable recording medium having a recorded program, for estimating a state in soil in a field.

BACKGROUND ART

Commonly, the production of agricultural products is performed based on the experience of the producer and intuition backed up by experience, and so it is difficult for an inexperienced producer to stably produce agricultural products. Also, even for a producer who has been engaged in agriculture for many years, there are cases where high yields are not stably produced. In order to develop the agriculture sector, it is required that producers be able to produce agricultural products stably.

Therefore, in recent years, in the agriculture sector, attempts have been made to support producers by utilizing IT technology. For example, Patent Document 1 proposes a system that automatically executes agricultural work based on sensor data from various sensors installed in a field, such as an illuminance sensor, a soil moisture sensor, and the like.

In the system disclosed in Patent Document 1, first, when dawn is detected by a signal from the illuminance sensor, irrigation performed prior to fertilization is executed, and further, fertilizer is administered to the field at each instance of a set time. Also, the system disclosed in Patent Document 1 specifies a moisture content of soil based on a signal from the soil moisture sensor, and executes irrigation according to the specified moisture content. Also note that irrigation is performed by operating a water supply pump installed in the field.

Also, commonly, in a field, there exist locations with good drainage and locations with poor drainage, so in order to accurately measure the soil moisture content in the field, it is necessary to install a soil moisture sensor at several locations in the field. In this case, the soil moisture content at a location where a soil moisture sensor has not been installed can be estimated by performing slope distribution of measured values of the soil moisture sensors that have been acquired. FIG. 11 illustrates slope distribution of measured values that have been measured by soil moisture sensors installed in a field.

LIST OF PRIOR ART DOCUMENTS

Patent Document

Patent Document 1: JP 2007-252234A

DISCLOSURE OF THE INVENTION

Problems to be Solved by the Invention

However, in order to measure the soil moisture content by the slope distribution described above, it is assumed that geographical features and soil quality in the field are uniform, and in a case where the geographical features and soil quality are not uniform, there is the problem that the estimated value becomes inaccurate. Also, ordinarily, in the field, there are slopes and irregularities, and there are various types of soil present, so it is common that the geographical features and the soil quality are not uniform. Also, there is a problem that estimation by slope distribution cannot be performed at a location that is not sandwiched between soil moisture sensors.

On the other hand, although it is conceivable that the above-described problems can be solved by increasing the number of soil moisture sensors to install, in this case, cost increases and also workability in the field decreases. In particular, as the size of the field increases, more agricultural work is carried out using a large agricultural machine, but with a large agricultural machine, work efficiency is greatly reduced by performing work while avoiding a plurality of soil moisture sensors. Also, there are cases where, in order to operate the agricultural machine, the sensors are withdrawn every time before starting work, and the sensors are reinserted after the work is finished, which may greatly reduce work efficiency.

An example object of the present invention is to provide a soil estimation device, a soil estimation method, and a computer-readable recording medium capable of improving estimation accuracy of the state in soil without increasing the number of sensors that detect the state in the soil, thereby solving the above-described problems.

Means for Solving the Problems

In order to attain the above object, a soil estimation device according to one aspect of the present invention includes an estimated model generation unit that, based on at least one among geographical information that specifies a geographical feature of a field of interest and soil distribution information that specifies a soil distribution in the field, generates an estimated model that estimates a state in soil from a measured value of the state in the soil of the field.

Also, in order to attain the above object, a soil estimation method according to one aspect of the present invention includes a step of, (a) based on at least one among geographical information that specifies a geographical feature of a field of interest and soil distribution information that specifies a soil distribution in the field, generating an estimated model that estimates a state in soil from a measured value of the state in the soil of the field.

Furthermore, in order to attain the above object, a computer-readable recording medium according to one aspect of the present invention has a recorded program including instructions causing a computer to execute a step of, (a) based on at least one among geographical information that specifies a geographical feature of a field of interest and soil distribution information that specifies a soil distribution in the field, generating an estimated model that estimates a state in soil from a measured value of the state in the soil of the field.

Advantageous Effects of the Invention

As described above, according to the present invention, it is possible to improve the estimation accuracy of the state in soil without increasing the number of sensors that detect the state in the soil.

BRIEF DESCRIPTION OF THE DRAWINGS

FIG. 6 is a diagram summarizing information related to each section according to an embodiment of the present invention.

MODE FOR CARRYING OUT THE INVENTION

Embodiment

Following is a description of a soil estimation device, a soil estimation method, and a program according to an embodiment of the present invention, with reference to FIGS. 1 to 10.

[Device Configuration]

Figure 1:
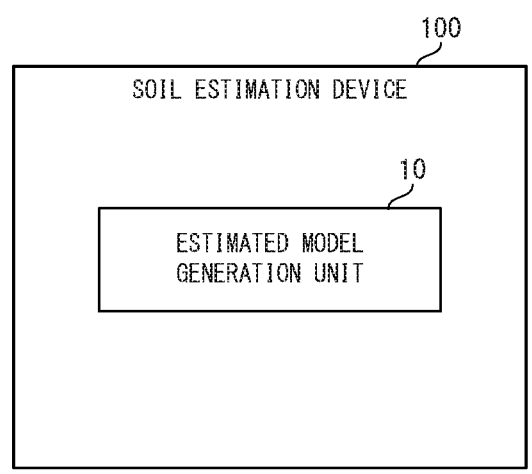
FIG. 1 is a block diagram showing a schematic configuration of a soil estimation device according to an embodiment of the present invention.

First, the configuration of the soil estimation device according to the present embodiment will be described. FIG. 1 is a block diagram showing a schematic configuration of the soil estimation device according to an embodiment of the present invention.

The soil estimation device 100 in the present embodiment shown in FIG. 1 is a device for estimating the state in soil in a field. The state in the soil is, for example, a state indicated by moisture content in the soil, nitrogen content, temperature, or the like.

As shown in FIG. 1, a soil estimation device 100 includes an estimated model generation unit 10. The estimated model generation unit 10 generates an estimated model based on at least one among geographical information that specifies a geographical feature of a field of interest (referred to below as an "interest field") and soil distribution information that specifies a soil distribution in the interest field. The estimated model is a model that estimates, from a measured value that indicates the state in the soil at one location within the interest field, the state in the soil at another location different than the one location. The geographical information is, for example, a geographical feature model that represents slopes or the like of the interest field. The soil distribution information is, for example, a soil distribution model that represents the soil distribution in the interest field.

In this way, in the present embodiment, the estimation model generation unit 10 generates an estimated model for estimating, in consideration of the geographical features and the soil quality of the field, from a measured value indicating the state in the soil at one location within the field, the state in the soil at another location different than the one location. Therefore, even in a case where the geographical features and the soil quality are not uniform in the field, it is possible to accurately estimate the state in the soil. Also, by this estimated model covering the entire field, if a measured value can be acquired from at least one location, the state in the soil in the entire field can be estimated. Therefore, according to the present embodiment, an increase in the number of sensors that detect the state in the soil is suppressed.

Figure 2:
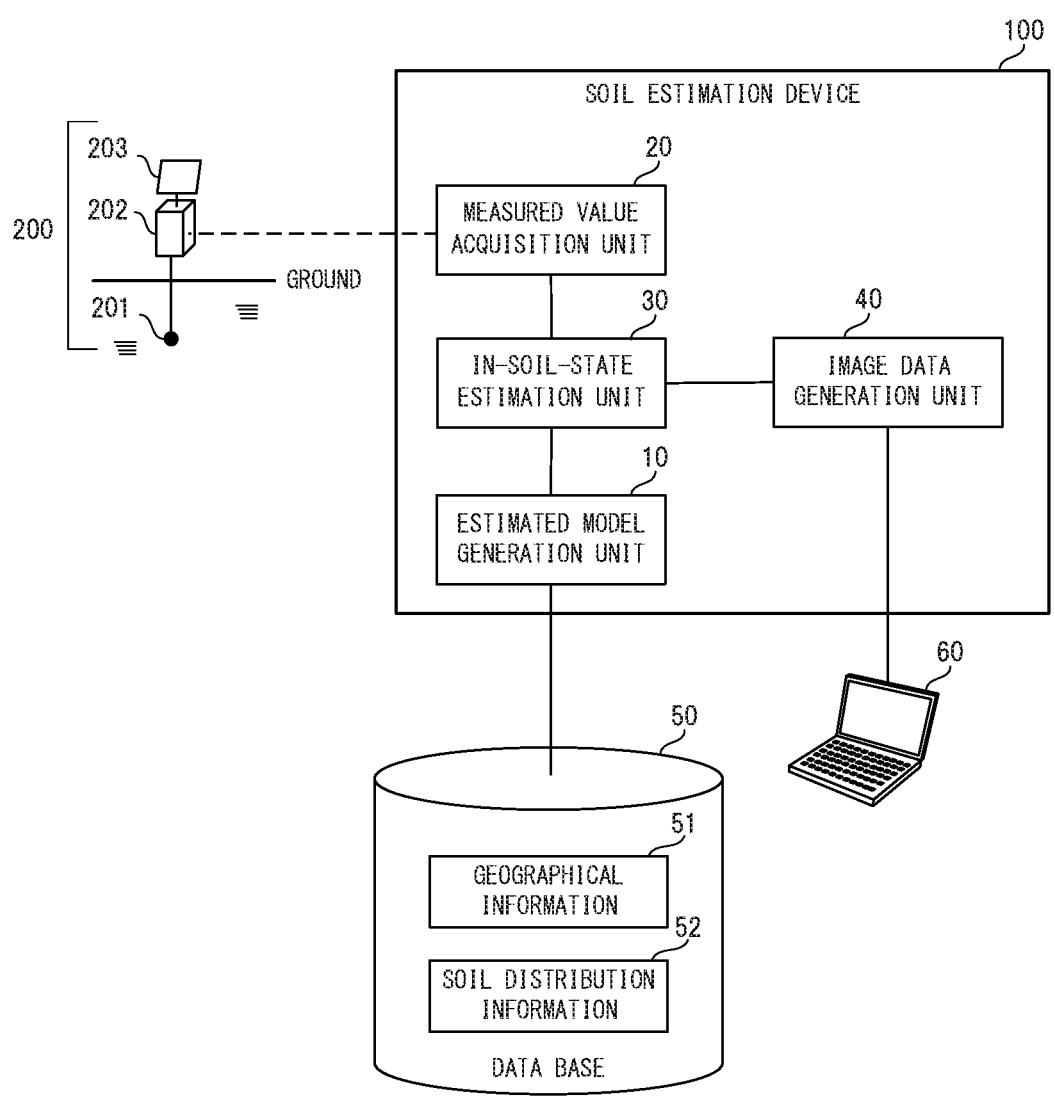
FIG. 2 is a block diagram showing a specific configuration of a soil estimation device according to an embodiment of the present invention.

Here, the configuration of the soil estimation device 100 according to the present embodiment will be described more specifically with reference to FIG. 2. FIG. 2 is a block diagram showing a specific configuration of a soil estimation device according to an embodiment of the present invention.

As shown in FIG. 2, in the present embodiment, the soil estimation device 100 includes, in addition to the estimated model generation unit 10, a measured value acquisition unit 20, an in-soil-state estimation unit 30, and an image data generation unit 40. Also, in the present embodiment, the soil estimation device 100 estimates the moisture content in soil as the state of the soil. Therefore, the estimated model is a model that estimates the amount of moisture in soil from a measured value of the moisture content in the soil, and the soil estimation device 100 is connected to a soil moisture sensor 200 installed in the field. The method of connecting the soil estimation device 100 and the soil moisture sensor 200 may be a wired connection or a wireless connection. Note that in FIG. 2, reference numeral 60 denotes a terminal device of an administrator.

The measured value acquisition unit 20 acquires a measured value that indicates the state in the soil of the interest field. Specifically, in the example shown in FIG. 2, the measured value acquisition unit 20 acquires a measured value of the moisture content in the soil from the soil moisture sensor 200. In the example shown in FIG. 2, the soil moisture sensor 200 mainly includes a sensor unit 201, an operation unit 202, and a solar cell 203.

Figure 5:
FIG. 5 is a diagram showing an example of sections set in a field according to an embodiment of the present invention.

Also, the soil moisture sensor 200 can be installed at an arbitrary position within the field, as shown in FIG. 5 to be described later. Furthermore, regarding the number of soil moisture sensors 200, it is sufficient that one soil moisture sensor 200 is installed in one field. Power may also be supplied to the soil moisture sensor 200 by a battery rather than by a solar cell.

The sensor unit 201 is buried under the ground, and detects moisture in the soil. The operation unit 202 calculates the moisture content in the soil from the detected moisture, and transmits data that specifies the calculated moisture content to the soil estimation device 100. The solar cell 203 supplies power to the sensor unit 201 and the operation unit 202. Note that the configuration of the soil moisture sensor 200 is not limited to the example shown in FIG. 2. It is sufficient that the soil moisture sensor 200 is capable of measuring the moisture content in the soil.

Also, in the present embodiment, the estimated model generation unit 10 first acquires geographical information 51 and soil distribution information 52 stored in the database 50. Note that a database 50 may be installed outside of the soil estimation device 100, or may be provided in the soil estimation device 100.

Figure 3:
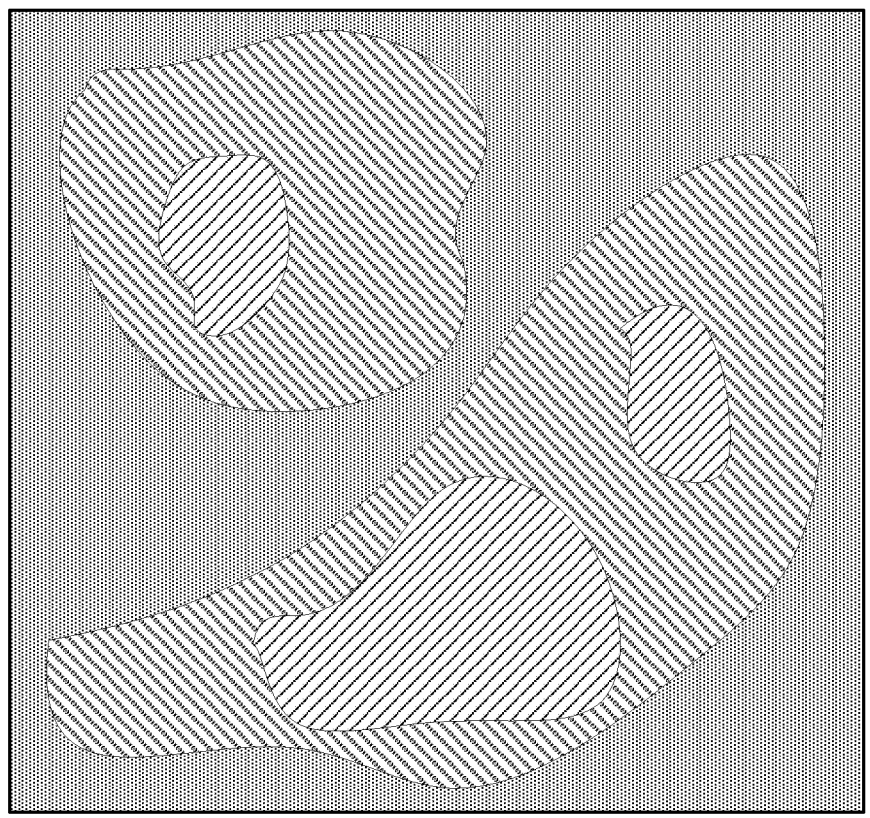
FIG. 3 is a diagram showing an example of geographical information used in an embodiment of the present invention.
Figure 3:
Figure 3:
Figure 3:
Figure 4:
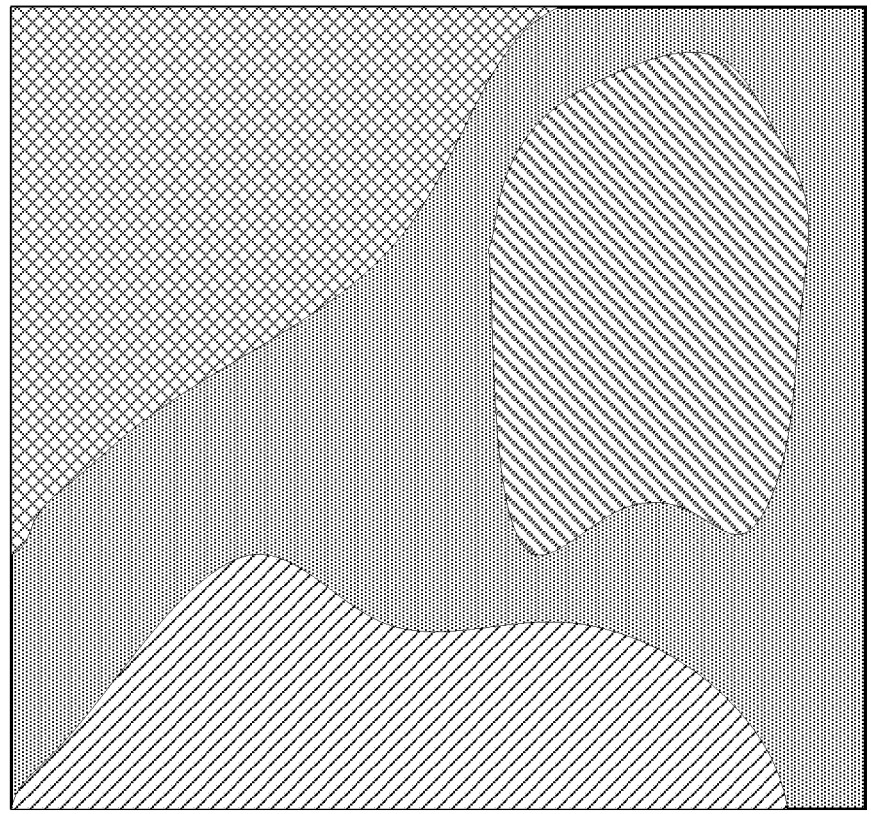
FIG. 4 is a diagram showing an example of soil distribution information used in an embodiment of the present invention.
Figure 4:
Figure 4:
Figure 4:
Figure 4:

Here, specific examples of the geographical information 51 and the soil distribution information 52 will be described with reference to FIGS. 3 and 4. FIG. 3 is a diagram showing an example of geographical information used in an embodiment of the present invention. In the example shown in FIG. 3, the geographical information expresses geographical features of the interest field with contour lines, and specifies the state of slopes of the surface of the interest field. Also, FIG. 4 is a diagram showing an example of soil distribution information used in an embodiment of the present invention. In the example shown in FIG. 4, the soil distribution information indicates regions corresponding to each composition of components, and specifies a distribution state of the components constituting the soil.

Furthermore, in order to generate an estimated model, the estimated model generation unit 10 divides the interest field into a plurality of parts and sets a plurality of sections, as shown in FIG. 5. That is, in order to generate an estimated model, the estimated model generation unit 10 virtually divides the interest field into a mesh form. FIG. 5 is a diagram showing an example of sections set in a field according to an embodiment of the present invention. In the example shown in FIG. 5, the estimated model generation unit 10 has set sections by dividing the interest field into a grid. The accuracy of the estimated model improves as the area of each section becomes smaller, that is, as the interest field is divided into a finer mesh.

Next, in the present embodiment, the estimated model generation unit 10 generates an estimated model by predicting an inflow amount and an outflow amount of moisture in the soil for each section based on both the geographical information 51 and the soil distribution information 52. At this time, in a case where geographical features of the interest field are uniform (flat) throughout the interest field, the estimated model generation unit 10 may use only the soil distribution information 52. On the other hand, in a case where the soil quality of the interest field is uniform throughout the interest field, the estimated model generation unit 10 may use only the geographical information 51. Also, at this time, the estimated model indicates the relative relationship of the moisture content in the soil in each section.

Specifically, the estimated model generation unit 10 first extracts the corresponding geographical information and soil distribution information for each section, and specifies the composition and slope of the soil in each section. Note that here, it is assumed that the area of the section set for the estimated model generation unit 10 to generate the estimated model equals the area of the section used when the in-soil-state estimation unit 30, described later, estimates the state in the soil, or alternatively, the area of the section set for the estimated model generation unit 10 to generate the estimated model is smaller than the area of the section used when the in-soil-state estimation unit 30 estimates the state in the soil.

In this case, when a plurality of parts having different compositions are included in one section, the estimated model generation unit 10 decides the composition in that section by taking into consideration the composition of each part and an area ratio between the parts. Also, when a plurality of regions having different heights are included in one section, the estimated model generation unit 10 decides the slope in that section by taking into consideration the height of each region and an area ratio between the regions.

Next the estimated model generation unit 10, for each section, generates an estimated model based on the specified soil composition and slope. In the present embodiment, the estimated model generation unit 10, for example, for each section, generates an estimated model by predicting an inflow amount and an outflow amount of moisture in the soil based on the specified soil composition and slope, and deriving a relative relationship of the moisture content in each section. Because each section is continuous, when predicting the inflow amount and the outflow amount of the moisture in the soil in a particular section, the inflow of moisture from an adjacent section and the outflow of moisture to an adjacent section are taken into consideration.

FIG. 6 is a diagram summarizing information related to each section. In the example shown in FIG. 6, sections are specified by a number in the vertical direction and a number in the horizontal direction shown in FIG. 5. Also, Silt (%), Sand (%), and Clay (%) are parameters that indicate the composition of the soil in the interest field, and are values calculated using the soil distribution information. Also, Slope (%) is a parameter that indicates the slope in the interest field, and is a value calculated using the geographical information. In the example shown in FIG. 5, a soil moisture sensor 200 is installed in a region that corresponds to a section 3-(3), so in the column "Measured Value" for the section 3-(3) shown in FIG. 6, a measured value is recorded.

The in-soil-state estimation unit 30 estimates the state in the soil for each section, using the measured value acquired by the measured value acquisition unit 20 and the estimated model. In the present embodiment, the in-soil-state estimation unit 30, by inputting the measured value to the estimated model generated by the estimated model generation unit 10, calculates an absolute value of the moisture content in each section from the relative relationship of the moisture content in each section.

In the example shown in FIG. 5, the in-soil-state estimation unit 30 estimates (calculates) the moisture content of a section where a sensor is not installed based on the measured value (300 mm) in the section 3-(3) where a sensor is installed, and the relative relationship between a steady state solution of the moisture content in the section 3-(3) and a steady state solution of the moisture content in the section where a sensor is not installed. Regarding the "Calculated Value" column in FIG. 6, a measured value is registered in a cell corresponding to a section where a sensor is installed, and a value of the moisture content that has been estimated by the in-soil-state estimation unit 30 is registered in a cell corresponding to a section where a sensor is not installed.

The in-soil-state estimation unit 30 is capable of dividing a field according to at least one of a degree of flatness of the field and a degree of uniformity of the soil distribution of the field. For example, when there is a high degree of flatness, there is a small amount of slope so the field is divided into large sections, and conversely, when there is a low degree of flatness, there is a large amount of slope so the field is divided into small sections. Also, in a location where the degree of uniformity of the soil distribution is high, the soil quality is constant so the field is divided into large sections, and conversely, when the degree of uniformity of the soil distribution is low, the soil quality is not constant so the field is divided into small sections. By adopting such a configuration, the in-soil-state estimation unit 30 is capable of conserving the amount of calculation required.

The image data generation unit 40, when the moisture content of each section is calculated by the in-soil-state estimation unit 30, generates image data for visualizing the moisture content in the soil. For example, as shown in FIG. 7, the image data generation unit 40 divides the field into a plurality of sections (blocks), creates a figure representing the moisture content in the soil of each block such that the moisture content in the soil of each block can be known at a glance, and generates image data of the created figure.

Figure 7:
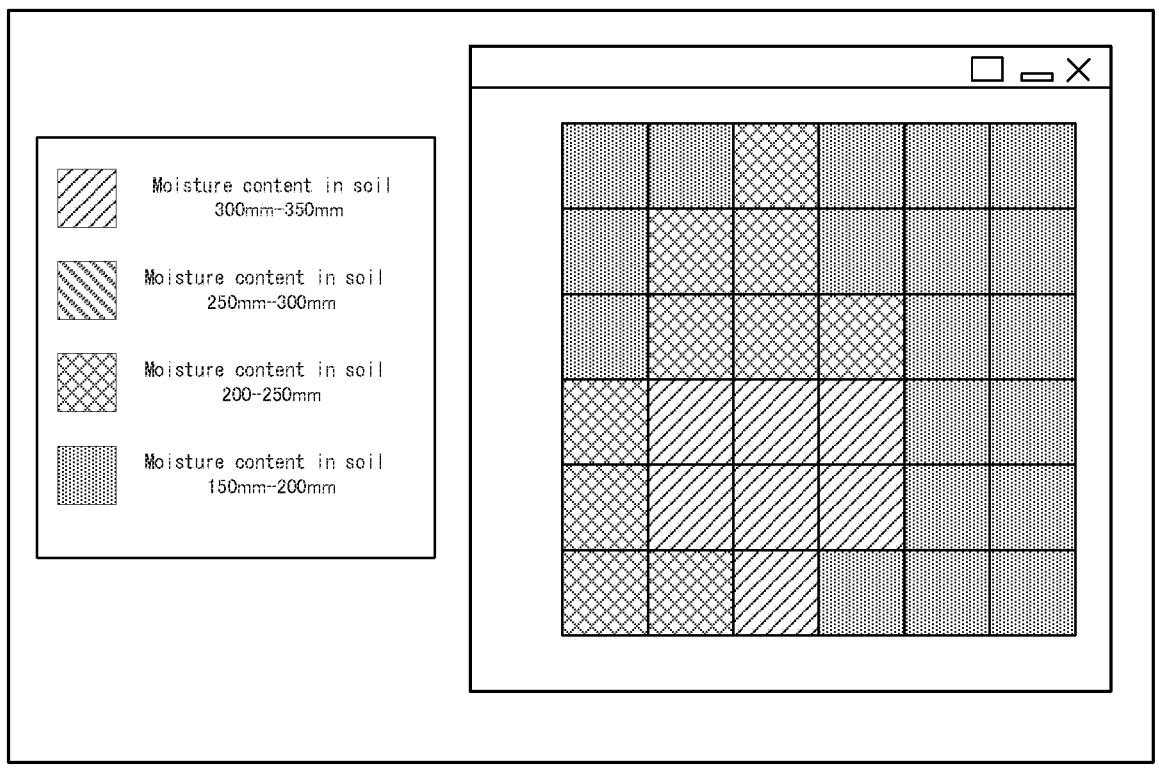
FIG. 7 is a diagram showing an example of an image generated according to an embodiment of the present invention.

The image data generation unit 40, as shown for example in FIG. 7, generates image data in which the patterns of respective blocks differ according to the moisture content. Also, the image data generation unit 40 can generate image data in which shades of color of respective blocks differ according to the moisture content. Note that the blocks set by the image data generation unit 40 may be the same as the sections set by the estimated model generation unit 10 or the sections set by the in-soil-state estimation unit 30, or the blocks may differ from those sections.

Also, in the present embodiment, it is not necessary for the blocks shown in FIG. 7 and the sections shown in FIG. 5 to be identical in size and number. The blocks shown in FIG. 7 may be set to a smaller number in the vertical direction and the horizontal direction than the sections shown in FIG. 5, or a plurality of sections may correspond to a single block. This is because the blocks shown in FIG. 7 are set in order to allow visualization, and when the blocks are set identical to the sections, there is a possibility that the size of the blocks will become too small and therefore difficult to view. Note that in this case, for example, an average value of the moisture content of a corresponding plurality of sections is used as the moisture content of one block.

Also, the image data generation unit 40 transmits the generated image data to the terminal device 60 of the administrator. Thus, the image shown in FIG. 7 is displayed on a screen of the terminal device 60. FIG. 7 is a diagram showing an example of an image generated according to an embodiment of the present invention.

[Device Operation]

Next, operation of the soil estimation device 100 according to the present embodiment will be described with reference to FIGS. 8 and 9. The following description will refer to FIGS. 1 to 7 as appropriate. Also, in the present embodiment, a soil estimation method is implemented by operating the soil estimation device 100. Therefore, the description of the soil estimation method in the present embodiment substitutes for the below description of operation of the soil estimation device 100.

First, processing to generate an estimated model will be described with reference to FIG. 8. FIG. 8 is a flowchart showing operation when an estimated model is generated by a soil estimation device according to an embodiment of the present invention.

Figure 8:
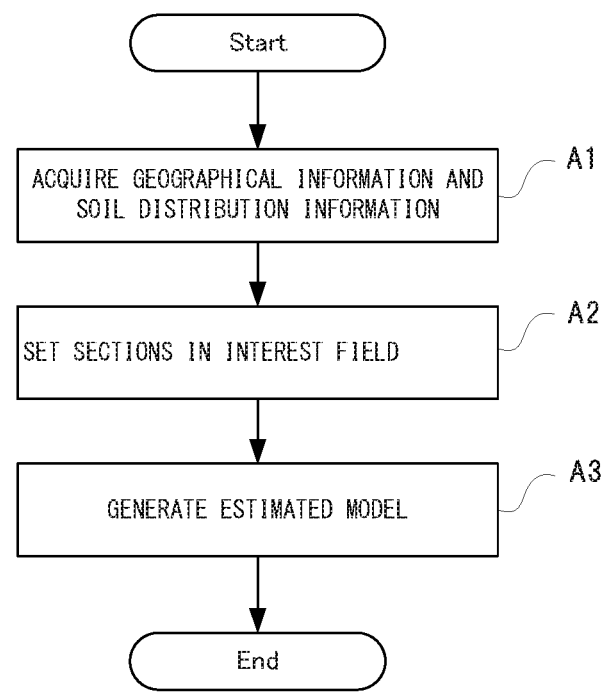
FIG. 8 is a flowchart showing operation when an estimated model is generated by a soil estimation device according to an embodiment of the present invention.

As shown in FIG. 8, first, the estimated model generation unit 10 accesses the database 50 and acquires the geographical information 51 and the soil distribution information 52 that are stored in the database 50 (Step A1).

Next, as shown in FIG. 5, the estimated model generation unit 10 divides the interest field into a plurality of parts and sets a plurality of sections (Step A2).

Next, the estimated model generation unit 10 generates an estimated model based on the geographical information 51 and the soil distribution information 52 that were acquired in Step A1 (Step A3).

Specifically, the estimated model generation unit 10, for each section, extracts the corresponding geographical information 51 and soil distribution information 52, and specifies the soil composition and slope in each section. Then the estimated model generation unit 10, for each section, uses the specified soil composition and slope to generate an estimated model. Also, the estimated model generation unit 10 stores the generated estimated models in the database 50.

Next, processing to estimate the moisture content in soil will be described with reference to FIG. 9. FIG. 9 is a flowchart showing operation when the moisture content in soil is estimated by a soil estimation device according to an embodiment of the present invention.

Figure 9:
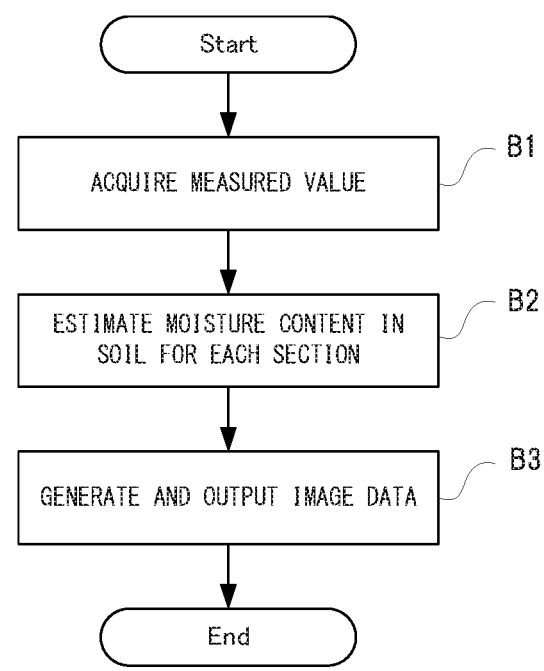
FIG. 9 is a flowchart showing operation when the moisture content in soil is estimated by a soil estimation device according to an embodiment of the present invention.

As shown in FIG. 9, first, the measured value acquisition unit 20 acquires a measured value of the moisture content in the soil from the soil moisture sensor 200 (Step B1).

Next, the in-soil-state estimation unit 30, using the measured value acquired in Step B1 and an estimated model, estimates the moisture content in the soil for each section (Step B2). Specifically, the in-soil-state estimation unit 30 inserts the measured value into the estimated model, and calculates the moisture content in each section.

Next, the image data generation unit 40 generates image data for visualizing the moisture content in the soil of the interest field estimated in Step B2, and outputs the generated image data to the terminal device 60 (Step B3). By executing Step B3, as shown in FIG. 7, a figure in which the moisture content in the soil of each section can be known at a glance is displayed on the screen of the terminal device 60.

Effects of the Embodiment

Figure 11:
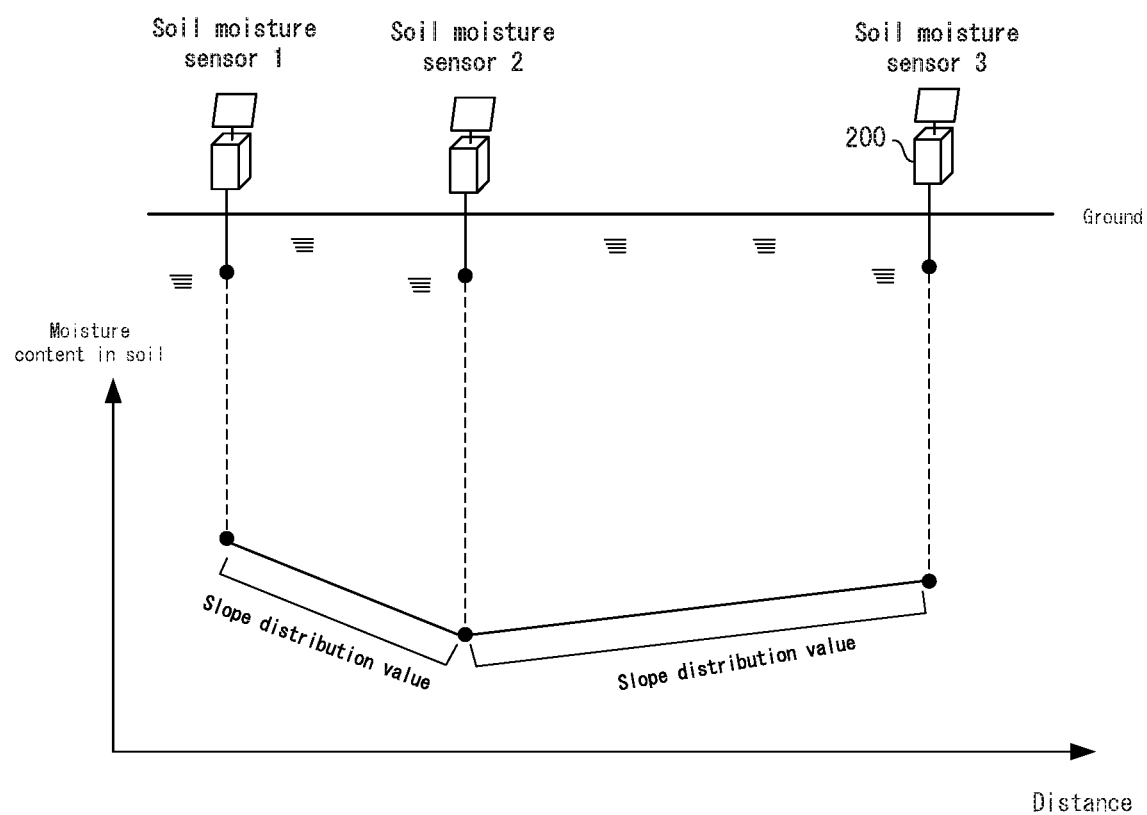
FIG. 11 is a diagram illustrating slope distribution of measured values measured by soil moisture sensors installed in a field.

As described above, according to the present embodiment, the moisture content in the soil is estimated using an estimated model that was generated in consideration of the geographical features and the soil quality of the field, so the accuracy of that estimation is significantly improved in comparison to a case where the conventional technique shown in FIG. 11 is used. Also, because it is possible to use only one sensor for measuring the measured value, a decrease in the work efficiency of agricultural work due to installing sensors is suppressed. Furthermore, in the present embodiment, the administrator can know the moisture content of the entire field from the screen of the administrator's own terminal device 60, so the administrator can easily manage the field.

In a case where the sections set when the estimated model generation unit 10 generates estimated models are made identical to the sections set when the in-soil-state estimation unit 30 estimates the moisture content in the soil, the estimated model generation unit 10, for each section, based on the specified soil composition and slope, can set an optimal calculation formula from among calculation formulas that have been set in advance. The calculation formulas mentioned here correspond to estimated models, and predict the inflow amount and the outflow amount of the moisture in the soil. The calculation formulas are set by performing experiments or the like in advance using soil samples having different compositions, and using the obtained experimental results. Also, the in-soil-state estimation unit 30, for each section, inserts a measured value into the selected calculation formula, and calculates the moisture content in each section.

[Program]

Regarding the program in present embodiment, it is sufficient that the program causes a computer to execute Steps A1 to A3 shown in FIG. 8, and Steps B1 to B3 shown in FIG. 9. By installing this program in the computer and executing the program, it is possible to realize the soil estimation device 100 and the soil estimation method in the present embodiment. In this case, a CPU (Central Processing Unit) of the computer functions as the estimated model generation unit 10, the measured value acquisition unit 20, the in-soil-state estimation unit 30, and the image data generation unit 40, and performs processing.

Also, the program in the present embodiment may be executed by a computer system constructed from a plurality of computers. In this case, for example, each computer may function as any of the estimated model generation unit 10, the measured value acquisition unit 20, the in-soil-state estimation unit 30, and the image data generation unit 40, respectively.

Figure 10:
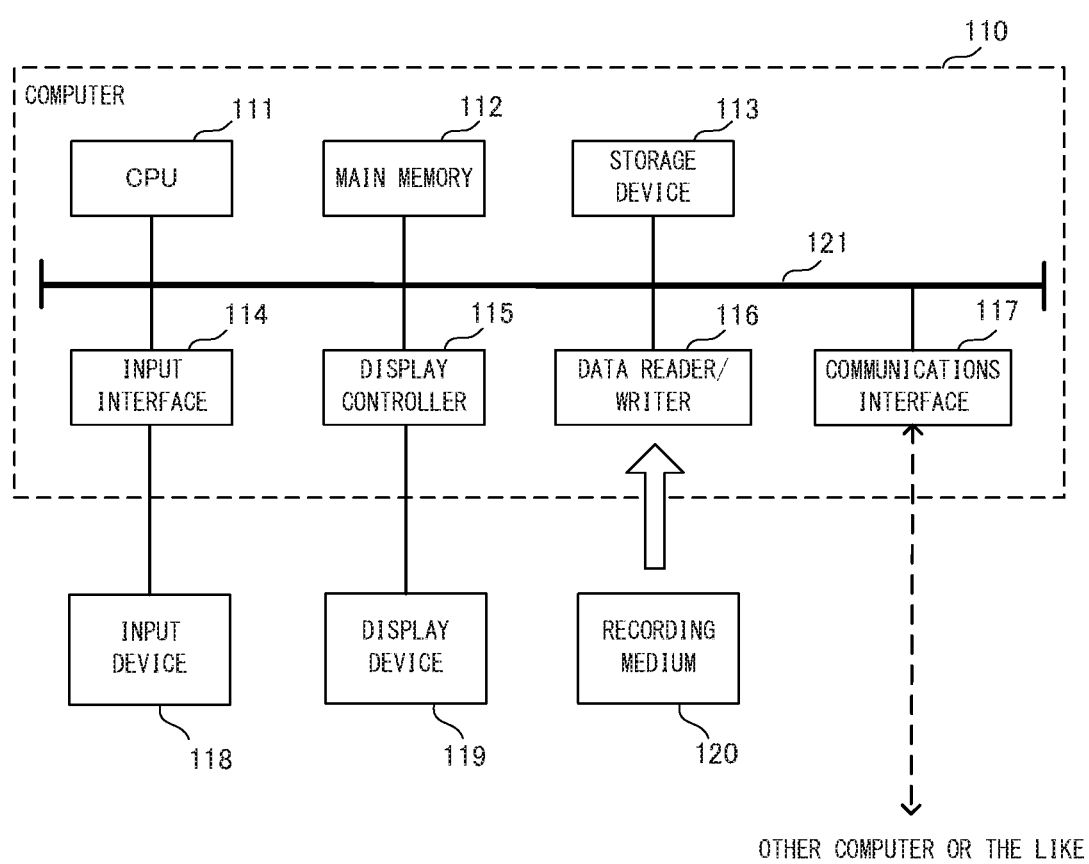
FIG. 10 is a block diagram showing an example of a computer that realizes a soil estimation device according to an embodiment of the present invention.

Here, a computer that realizes the soil estimation device 100 by executing the program according to the present embodiment will be described with reference to FIG. 10. FIG. 10 is a block diagram showing an example of a computer that realizes a soil estimation device according to an embodiment of the present invention.

As shown in FIG. 10, a computer 110 includes a CPU 111, a main memory 112, a storage device 113, an input interface 114, a display controller 115, a data reader/writer 116, and a communications interface 117. These units are each connected through a bus 121 so as to be capable of performing data communications with each other.

The CPU 111 opens the program (code) according to the present embodiment, which is stored in the storage device 113, into the main memory 112 and executes the program in a predetermined order, thereby executing various operations. The main memory 112 is typically a volatile storage device such as a DRAM (Dynamic Random Access Memory). Also, the program according to the present embodiment is provided in a state stored on a computer-readable recording medium 120. Note that the program according to the present embodiment may be distributed on an internet connected through the communications interface 117.

Also, a specific example of the storage device 113 includes, other than a hard disk drive, a semiconductor storage device such as a flash memory. The input interface 114 mediates data transmission between the CPU 111 and an input device 118, for example a keyboard and a mouse. The display controller 115 is connected to a display device 119 and controls display on the display device 119.

The data reader/writer 116 mediates data transmission between the CPU 111 and the recording medium 120, reads the program from the recording medium 120, and writes processing results in the computer 110 to the recording medium 120. The communications interface 117 mediates data transmission between the CPU 111 and other computers.

Also, specific examples of the recording medium 120 include a general-purpose semiconductor storage device such as a CF (Compact Flash (registered trademark)) device and an SD (Secure Digital) device, a magnetic recording medium such as a flexible disk (Flexible Disk), an optical recording medium such as a CD-ROM (Compact Disk Read Only Memory), and the like.

Note that the soil estimation device 100 according to the present embodiment can be realized not only by a computer having a program installed, but also by using hardware corresponding to each part. Further, a configuration may be adopted in which a portion of the soil estimation device 100 is realized by a program, and the remaining portions are realized by hardware.

Some portion or all of the embodiment described above can be realized according to (Supplementary Note 1) to (Supplementary Note 18) described below, but the below description does not limit the invention.

(Supplementary Note 1)

A soil estimation device, comprising:

an estimated model generation unit that, based on at least one among geographical information that specifies a geographical feature of a field of interest and soil distribution information that specifies a soil distribution in the field, generates an estimated model;

wherein the estimated model is a model that estimates, from a measured value that indicates the state in the soil at one location within the field, the state in the soil at another location different than the one location.

(Supplementary Note 2)

The soil estimation device according to Supplementary Note 1, wherein the estimated model generation unit, for each section obtained by dividing the field into a plurality of parts, predicts an inflow amount and an outflow amount of moisture in the soil, and generates the estimated model indicating a relative relationship of moisture content in the soil in each section.

(Supplementary Note 3)

The soil estimation device according to Supplementary Note 2, further comprising:

a measured value acquisition unit that acquires the measured value of the moisture in the soil of the field;

an in-soil-state estimation unit that, using the measured value that was acquired and the estimated model, estimates the moisture content in the soil; and an image data generation unit that generates image data for visualizing the estimated moisture content in the soil.

(Supplementary Note 4)

The soil estimation device according to Supplementary Note 3, wherein the image data generation unit generates the image data such that for each block obtained by dividing the field into a plurality of parts, a pattern in the block differs according to the moisture content.

(Supplementary Note 5)

The soil estimation device according to Supplementary Note 3 or 4, wherein the image data generation unit generates image data in which, for each block obtained by dividing the field into a plurality of parts, a shade of color in the block is represented according to the moisture content.

(Supplementary Note 6)

The soil estimation device according to any one of Supplementary Notes 1 to 5, wherein the geographical information is information that specifies a state of a slope of a surface of the field, and the soil distribution information is information that specifies a distribution state of a component that constitutes the soil.

(Supplementary Note 7)

A soil estimation method, comprising:

(a) a step of, based on at least one among geographical information that specifies a geographical feature of a field of interest and soil distribution information that specifies a soil distribution in the field, generating an estimated model;

wherein the estimated model is a model that estimates, from a measured value that indicates the state in the soil at one location within the field, the state in the soil at another location different than the one location.

(Supplementary Note 8)

The soil estimation method according to Supplementary Note 7, wherein the step (a) includes, for each section obtained by dividing the field into a plurality of parts, predicting an inflow amount and an outflow amount of moisture in the soil, and generating the estimated model indicating a relative relationship of moisture content in the soil in each section.

(Supplementary Note 9)

The soil estimation method according to Supplementary Note 8, further comprising:

(b) a step of acquiring the measured value of the moisture in the soil of the field;

(c) a step of, using the measured value that was acquired in the step (b) and the estimated model that was generated in the step (a), estimating the moisture content in the soil; and (d) a step of generating image data for visualizing the estimated moisture content in the soil.

(Supplementary Note 10)

The soil estimation method according to Supplementary Note 9, wherein in the step (d), the image data is generated such that for each block obtained by dividing the field into a plurality of parts, a pattern in the block differs according to the moisture content.

(Supplementary Note 11)

The soil estimation method according to Supplementary Note 9 or 10, wherein in the step (d), image data is generated in which, for each block obtained by dividing the field into a plurality of parts, a shade of color in the block is represented according to the moisture content.

(Supplementary Note 12)

The soil estimation method according to any one of Supplementary Notes 7 to 11, wherein the geographical information is information that specifies a state of a slope of a surface of the field, and the soil distribution information is information that specifies a distribution state of a component that constitutes the soil.

(Supplementary Note 13)

A computer-readable recording medium having a recorded program including a command causing a computer to execute:

(a) a step of, based on at least one among geographical information that specifies a geographical feature of a field of interest and soil distribution information that specifies a soil distribution in the field, generating an estimated model;

wherein the estimated model is a model that estimates, from a measured value that indicates the state in the soil at one location within the field, the state in the soil at another location different than the one location.

(Supplementary Note 14)

The computer-readable recording medium according to Supplementary Note 13, wherein the step (a) includes, for each section obtained by dividing the field into a plurality of parts, predicting an inflow amount and an outflow amount of moisture in the soil, and generating the estimated model indicating a relative relationship of moisture content in the soil in each section.

(Supplementary Note 15)

The computer-readable recording medium according to Supplementary Note 14, including commands further causing the computer to execute:

(b) a step of acquiring the measured value of the moisture in the soil of the field;

(c) a step of, using the measured value that was acquired in the step (b) and the estimated model that was generated in the step (a), estimating the moisture content in the soil for each of the sections; and (d) a step of generating image data for visualizing the moisture content in the soil estimated for each of the sections.

(Supplementary Note 16)

The computer-readable recording medium according to Supplementary Note 15, wherein in the step (d), the image data is generated such that for each block obtained by dividing the field into a plurality of parts, a pattern in the block differs according to the moisture content.

(Supplementary Note 17)

The computer-readable recording medium according to Supplementary Note 15 or 16, wherein in the step (d), image data is generated in which, for each block obtained by dividing the field into a plurality of parts, a shade of color in the block is represented according to the moisture content.

(Supplementary Note 18)

The computer-readable recording medium according to any one of Supplementary Notes 13 to 17, wherein the geographical information is information that specifies a state of a slope of a surface of the field, and the soil distribution information is information that specifies a distribution state of a component that constitutes the soil.

Although the present invention is described above with reference to embodiments, the present invention is not limited by the above embodiments. Within the scope of the present invention, various modifications understandable by those skilled in the art can be made to the configurations or details of the present invention.

INDUSTRIAL APPLICABILITY

As described above, according to the present invention, it is possible to improve the accuracy of estimation of the state in soil without increasing the number of sensors that detect the state in the soil. The present invention is useful in sectors requiring detection of a state in soil, particularly the agriculture sector.

DESCRIPTION OF REFERENCE SIGNS

10 Estimated model generation unit
20 Measured value acquisition unit
30 In-soil-state estimation unit
40 Image data generation unit
50 Database
51 Geographical information
52 Soil distribution information
60 Terminal device
100 Soil estimation device
110 Computer
111 CPU
112 Main memory
113 Storage device
114 Input interface
115 Display controller
116 Data reader/writer
117 Communications interface
118 Input device 119 Display device
120 Recording medium
121 Bus
200 Soil moisture sensor
201 Sensor unit
202 Operation unit
203 Solar cell

The invention claimed is:

1. A soil estimation device, comprising:
   at least one memory storing instructions; and
   at least one processor configured to execute the instructions to:
   generate an estimated model based on at least one from among geographical information that specifies a geographical feature of a field of interest and soil distribution information that specifies a soil distribution in the field;
   estimate, from a measured value that indicates a state in soil at one location within the field, a state in the soil at another location different from the one location; and
   predict an inflow amount and an outflow amount of moisture in the soil for each section obtained by dividing the field into a plurality of parts, and generate the estimated model indicating a relative relationship of moisture content in the soil in each section.

2. The soil estimation device according to claim 1, wherein the at least one processor is further configured to:
   acquire the measured value of the moisture in the soil of the field;
   based on the measured value and the estimated model, estimate the moisture content in the soil; and
   generate image data for visualizing the estimated moisture content in the soil.

3. The soil estimation device according to claim 2,
   wherein the at least one processor is further configured to generate the image data such that, for each block obtained by dividing the field into the plurality of parts, a pattern in the block differs according to the moisture content.

4. The soil estimation device according to claim 2,
   wherein the at least one processor is further configured to generate image data in which, for each block obtained by dividing the field into the plurality of parts, a shade of color in the block is represented according to the moisture content.

5. The soil estimation device according to claim 1,
   wherein the geographical information is information that specifies a state of a slope of a surface of the field, and
   the soil distribution information is information that specifies a distribution state of a component that constitutes the soil.

6. A soil estimation method, performed by a computer, the method comprising:
   generate an estimated model based on at least one from among geographical information that specifies a geographical feature of a field of interest and soil distribution information that specifies a soil distribution in the field;
   based on the estimated model, estimating, from a measured value that indicates a state in a soil at one location within the field, a state in the soil at another location different from the one location; and
   predicting an inflow amount and an outflow amount of moisture in the soil for each section obtained by dividing the field into a plurality of parts, and generate the estimated model indicating a relative relationship of moisture content in the soil in each section.

7. A non-transitory computer-readable recording medium having recorded thereon a computer program including a command causing a computer to:
   generate an estimated model based on at least one from among geographical information that specifies a geographical feature of a field of interest and soil distribution information that specifies a soil distribution in the field;
   based on the estimated model, estimate, from a measured value that indicates a state in the soil at one location within the field, a state in the soil at another location different from the one location; and
   predict an inflow amount and an outflow amount of moisture in the soil for each section obtained by dividing the field into a plurality of parts, and generate the estimated model indicating a relative relationship of moisture content in the soil in each section.

* * * * *